US005726906A

United States Patent [19]
Matthiessen et al.

[11] Patent Number: 5,726,906
[45] Date of Patent: Mar. 10, 1998

[54] METHOD OF DETERMINING THE PORTION OF AN ELECTROCHEMICALLY CONVERTIBLE SUBSTANCE IN A GAS SAMPLE

[75] Inventors: Hans Matthiessen; Gero Sagasser, both of Bad Schwartau, Germany

[73] Assignee: Drägerwerk Aktiengesellschaft, Lübeck, Germany

[21] Appl. No.: 560,486

[22] Filed: Nov. 17, 1995

[30] Foreign Application Priority Data

Nov. 19, 1994 [DE] Germany .......................... 44 41 205.3

[51] Int. Cl.$^6$ ...................................................... G06G 7/19
[52] U.S. Cl. ........................................... 364/497; 73/19.01
[58] Field of Search .......................... 364/496, 497, 364/498, 499, 570, 571.02; 73/19.01, 23.2, 23.21, 23.3; 422/83, 84, 98, 119; 436/900; 128/719

[56] References Cited

U.S. PATENT DOCUMENTS

| 4,770,026 | 9/1988 | Wolf . | |
| 5,048,321 | 9/1991 | Chow | 73/23.3 X |
| 5,612,896 | 3/1997 | Stock | 364/496 |

FOREIGN PATENT DOCUMENTS

| 4327312 | 2/1994 | Germany . |
| 2285136 | 6/1995 | United Kingdom . |

*Primary Examiner*—James P. Trammell
*Assistant Examiner*—M. Kemper
*Attorney, Agent, or Firm*—Walter Ottesen

[57] ABSTRACT

A method for determining the portion of an electrochemically detectable substance in a gas sample includes the steps of introducing the gas sample into an electrochemical measuring cell 1 and generating a measurement curve i(t) by the electrochemical conversion of the substance in the measuring cell 1. The measuring curve i(t) increases from a reference line to a maximum value $i_{max}$ and drops back again to the reference line. Then, the maximum value $i_{max}$ and an area A below the measuring curve i(t) are determined. The area A is proportional to the portion of the substance in the gas sample. The method is improved in that a new measurement value is made available after a short time. This is achieved in that the maximum value $i_{n\ max}$ and the area $A_n$ of a previous measurement are compared to each other and a proportionality factor $K_n$ is determined. The proportionality factor $K_n$ is given by the ratio of the area $A_n$ to the maximum value $i_{n\ max}$ and, for a new measurement, a new maximum value $i_{n+1\ max}$ is determined and the portion of the substance in the gas sample is computed for the new measurement from the new maximum value $i_{n+1\ max}$ and the proportionality factor $K_n$ of the previous measurement.

2 Claims, 2 Drawing Sheets

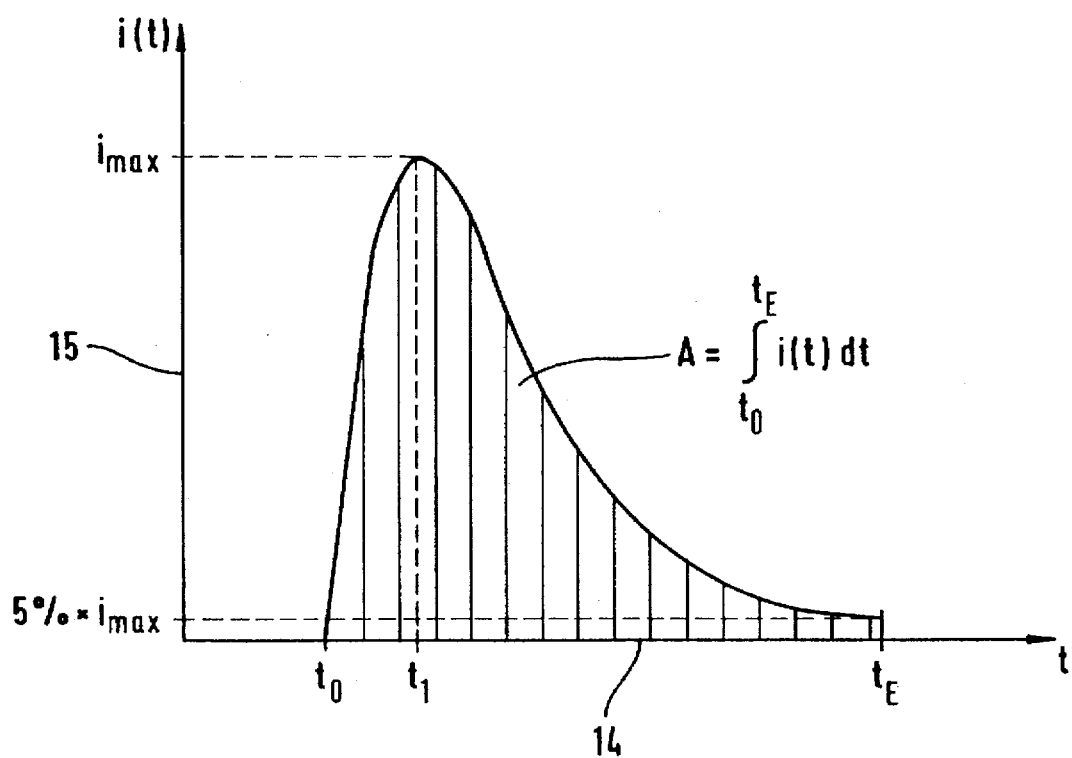

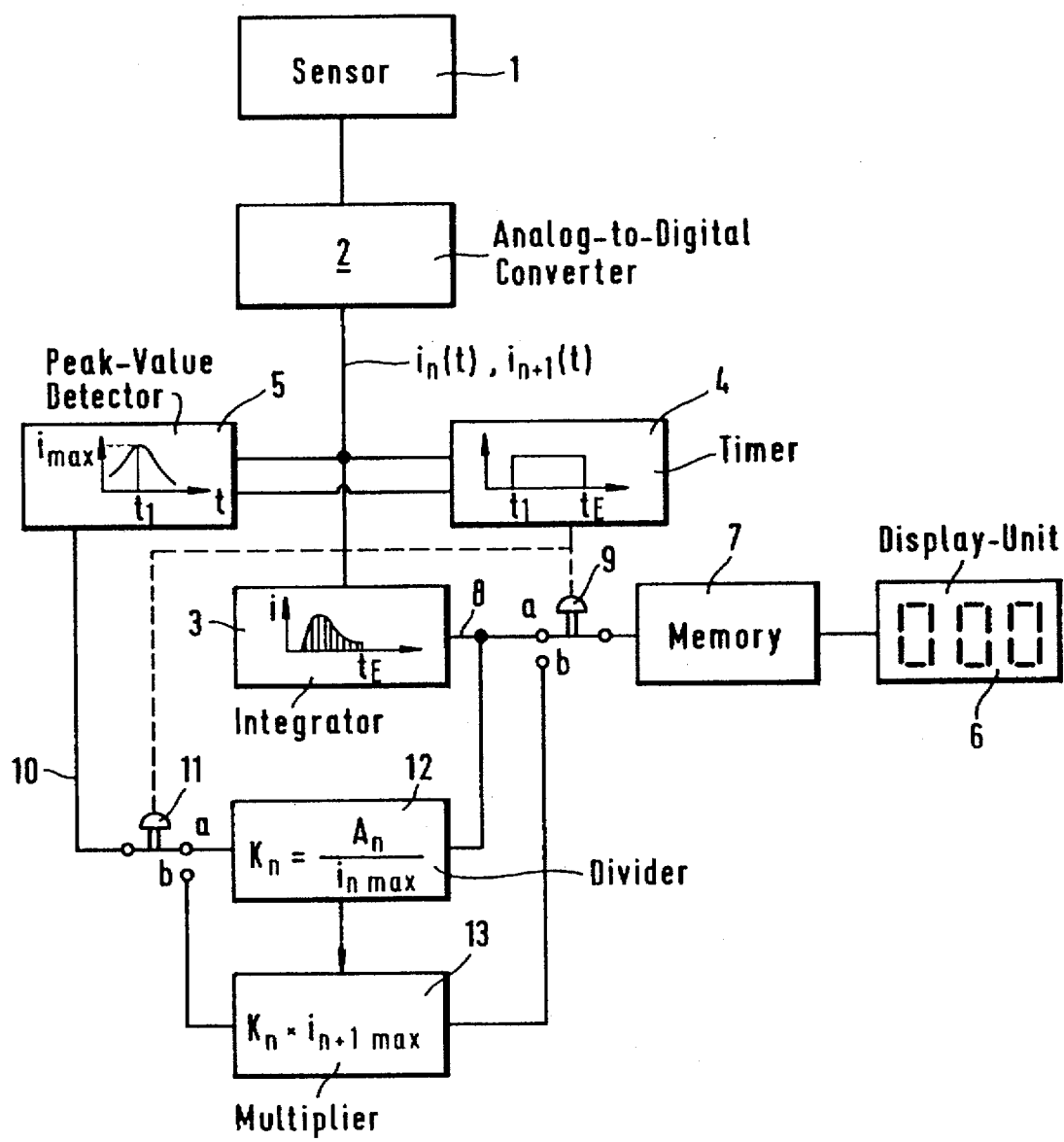

METHOD OF DETERMINING THE PORTION OF AN ELECTROCHEMICALLY CONVERTIBLE SUBSTANCE IN A GAS SAMPLE

FIELD OF THE INVENTION

The invention relates to a method for determining the portion of an electrochemically detectable substance in a gas sample. The method includes the steps of: introducing the gas sample into an electrochemical measuring cell wherein the substance is electrochemically converted; generating a measurement curve from the conversion which measurement curve increases from a reference line to a maximum value and then drops back again to the reference line; and, determining a maximum value of the measurement curve and the area below the measurement curve which is proportional to the portion of the substance in the gas sample.

BACKGROUND OF THE INVENTION

An arrangement for quantitatively determining an electrochemically detectable substance in a gas sample is disclosed in published German patent application 4,327,312, (corresponds to U.S. patent application Ser. No. 07/931,069, filed Aug. 17, 1992). With this known arrangement, the concentration of breath alcohol is determined in that a breath gas sample is introduced into a fuel cell and a current flow i(t) is generated by the oxidation of the alcohol. The current curve resulting from the conversion of the alcohol molecules at first increases to a maximum value $i_{max}$ and then drops back to the initial value.

In the following, the current curve is referred to as the measurement curve. In the known method, the concentration of the substance in the gas sample is determined from the area below the measurement curve while introducing calibration values. Although the determination of the concentration by evaluating the area below the measurement curve is relatively precise, it does, however, take too long for many applications. In the known arrangement, the evaluation time is shortened in that first two points of the measurement curve are identified and the trace of the curve is approximated by a log-normal distribution curve. One of these two points is the maximum value of the measurement curve; whereas, the selection of the second point is dependent upon the desired accuracy of the area determination. If, as the second point, a measurement value is selected just after exceeding the maximum value of the measurement curve, then the accuracy of the area determination is reduced. If, however, the second point is selected at a significantly later time point, then the accuracy of the area determination is increased. The time saved compared to the complete evaluation of the area below the measurement curve is reduced for this case.

The approximation of the measurement curve by a log-normal distribution furthermore has the precondition that the true measurement curve of the measuring cell does not differ significantly over the time of use from this special function trace. The deviations of the true measurement curve from the log-normal distribution curve are possibly within the tolerable limits viewed statistically. However, no clear statement can be obtained as to the performance of an individual measuring cell. Furthermore, in the known evaluation method, a measurement value is available, at the earliest, after a drop of the measurement curve to approximately 66% of the maximum value.

U.S. Pat. No. 4,770,026 discloses that the concentration of alcohol molecules in a gas sample can be determined exclusively from the maximum value of the measurement curve of an electrochemical measuring cell. Although the maximum value of the measurement curve is available quickly, it is, however, greatly dependent upon the temperature and the deterioration of the measuring cell and is therefore too imprecise as a measurement value for the determination of concentration.

SUMMARY OF THE INVENTION

It is an object of the invention to improve the method utilizing a measuring cell of the kind described above by making an alcohol concentration measurement value available after a shorter evaluation time.

The method according to the invention includes the steps of: comparing the maximum value and the area of a measurement curve of a previous measurement to each other; determining a proportional factor given by the ratio of the maximum value and the area; determining a new maximum value for a new measurement; and, computing the portion of the substance in the gas sample for the new measurement from the new maximum value and the proportionality factor of the previous measurement.

The advantage of the invention is seen essentially in that the concentration portion of the substance, which is to be detected, in the gas sample is determined from a corrected maximum value of the measurement curve. This maximum value is available after a short evaluation time span. In the present case, the correction factor for the maximum value is identified as the proportionality factor and is determined during a previous measurement. The proportionality factor is computed anew for each measurement from the area A below the measurement curve and the maximum value $i_{max}$ of the measurement curve. In the measuring method according to the invention, the concentration measurement value is available after a short time; whereas, the proportionality factor, which is necessary for the determination of the new concentration measurement value, was determined already during the previous measurement.

The evaluation time can be shortened still further if mean values are formed from the individual proportionality factors so that, for the case of a previous measurement wherein the evaluation of the area integral (that is, the determination of the area below the measurement curve) was not waited for, a proportionality factor is nonetheless available via the mean value formation. From the time-dependent change of the proportionality factor, conclusions can be drawn as to the deterioration of performance of the measuring cell. Limit values can also be set for the proportionality factor. An exchange of the measuring cell can be displayed to the user with these limit values.

A new area is advantageously determined from the measurement curve of a new measurement. A new proportionality factor is determined together with the new maximum value.

BRIEF DESCRIPTION OF THE DRAWINGS

The invention will now be described with reference to the drawings wherein:

FIG. 1 shows a time-dependent trace of the sensor current i(t) of an electrochemical measuring cell; and, FIG. 2 shows a schematic block diagram for carrying out an embodiment of the method according to the invention.

DESCRIPTION OF THE PREFERRED EMBODIMENTS OF THE INVENTION

FIG. 1 shows a time-dependent trace of the sensor current i(t) of an electrochemical measuring cell not shown in FIG.

1. The time-dependent trace is shown for the measuring cell subjected to a charge of a gas sample containing alcohol molecules. The time (t) is plotted along the abscissa 14 of the coordinate system shown in FIG. 1 and the sensor current i(t) is plotted along the ordinate 15. At time point $t=t_0$, the measuring cell is charged with alcohol vapor whereupon the sensor current i(t) increases to the maximum value $i_{max}$ at time point $t=t_1$ and drops again in the direction of the original value in correspondence to the extent of the electrochemical conversion. In the following, the curve of sensor current i(t) as a function of time (t) is referred to as the measurement curve.

A value proportional to the concentration portion of the alcohol molecules in the gas sample results from a determination of the area A below the measurement curve i(t). The time interval wherein the area is determined lies between the time point from the start of charging the measuring cell with gas (at time $t=t_0$) to the drop of the measurement curve to approximately 5% of the maximum value $i_{max}$ at time point $t=t_E$. For simplification, it is assumed that the reference line necessary for the integration is coincident with the abscissa 14. Limiting the integration interval to the time point $t=t_E$ (that is, drop to 5% of the maximum value $i_{max}$) has more practical reasons, namely, to limit the duration of the integration because the measurement curve i(t) approaches the reference line asymptotically.

In FIG. 2, the method of the invention is shown in the form of the block circuit diagram.

An electrochemical sensor 1 is connected via an analog-to-digital converter 2 to an integrator 3 which evaluates the time-dependent trace of the sensor current i(t) as a measurement curve and determines the area A below the measurement curve between $t=t_0$ and $t=t_E$. The sensor current i(t) is additionally supplied to a timer 4 and a peak-value detector 5. The peak-value detector 5 determines the maximum value $i_{max}$ of the measurement curve i(t). The value determined by the integrator 3 for the area A of the measurement curve is proportional to the number of alcohol molecules in the gas sample. The alcohol concentration measurement value is displayed on a display unit 6 and results from a comparison of the area A to a calibration table having concordance values for the area A and the alcohol concentration. The calibration table is stored in a memory 7.

A first switch 9 is connected into a signal line 8 between the integrator 3 and the memory 7. A second switch 11 is connected into a signal line 10 which transmits the maximum value $i_{max}$ of the peak-value detector 5. The second switch 11 is connected to a divider 12. The signal line 8 is also connected to the divider 12 and a measuring signal proportional to the area A is transmitted on the signal line 8.

The free switch contacts (b) of switches (9, 11) are connected to a multiplier 13. A proportionality factor $K_n$ is determined in the divider 12 as the quotient of the area $A_n$ and the maximum value $i_n$ max of a (n)-th measurement. The multiplier 13 forms the product of the proportionality factor $K_n$ of the (n)-th measurement and the maximum value $i_{n+1}$ max of the measurement curve of the (n+1)-th measurement.

The switches (9, 11) are actuated by means of the timer 4 in such a manner that they are switched from the switch position (a) to the switch position (b) during the time span between $t_1$ and $t_E$. In FIG. 2, the switch position (a) of the switches (9, 11) is shown.

The operation of the method according to the invention is explained below:

The sensor 1 is charged with a gas sample to be measured and generates a measurement curve $i_n(t)$. In the integrator 3, a corresponding area $A_n$ is computed for the measurement curve $i_n(t)$ between the integration limits $t_0$ and $t_E$. The maximum value $i_{n\ max}$ corresponding to the measurement curve $i_n(t)$ is determined in the peak-value detector 5 for the time point $t=t_1$ and switched via the second switch 11 to the divider 12. In the divider 12, a proportionality factor $K_n$ of the (n)-th measurement is formed from the quotient of $A_n$ and $i_{n\ max}$ and stored in the divider 12. When taking a sample following the (n)-th measurement (that is, the (n+1)-th measurement), a new area $A_{n+1}$ and a new maximum value $i_{n+1\ max}$ are formed. The concentration portion of the substance to be detected in the gas sample is determined from the area $A_{n+1}$ of the (n+1)-th measurement at time point $t=t_E$.

The invention comprises displaying this concentration measurement value with slightly reduced precision already significantly earlier, that is, at time point $t=t_1$ at which the measurement curve $i_{n+1}(t)$ has reached its maximum value $i_{n+1\ max}$. For this purpose, at time point $t=t_1$, (when the maximum value $i_{n+1\ max}$ is determined), the switches (9, 11) are switched to the switch position (b) and, in the multiplier 13, the product of the proportionality factor $K_n$ of the (n)-th measurement and the maximum value $i_{n+1\ max}$ of the (n+1)-th measurement is displayed while taking into account the calibration values of the memory 7.

At time point $t=t_E$, the switches (9, 11) are again switched back into the switch position (a) and the precise alcohol concentration measurement value can be displayed via the evaluation of the complete area $A_{n+1}$. A new proportionality factor $K_{n+1}$ for the (n+2)-th measurement can be computed in the divider 12 from the area $A_{n+1}$ and the maximum value $i_{n+1\ max}$ of the (n+1)-th measurement. The new proportionality factor $K_{n+1}$ can then be stored.

It is understood that the foregoing description is that of the preferred embodiments of the invention and that various changes and modifications may be made thereto without departing from the spirit and scope of the invention as defined in the appended claims.

What is claimed is:

1. A method of determining the portion of an electrochemically detectable substance in a gas sample, the method comprising the steps of:

introducing the gas sample into an electrochemical measuring cell wherein the substance is electrochemically converted to make a (n)-th measurement;

generating a (n)-th measurement curve i(t) from the electrochemical conversion with said (n)-th measurement curve i(t) increasing from a reference line to a (n)-th maximum value $i_{n\ max}$ and then falling off to said reference line;

determining said (n)-th maximum value $i_{n\ max}$ and an area $A_n$ below said (n)-th measurement curve i(t) which is proportional to the portion of said substance in said gas sample;

comparing said (n)-th maximum value $i_{n\ max}$ to said area $A_n$;

determining a proportionality factor $K_n$ giving the ratio of said area $A_n$ to said maximum value $i_{n\ max}$ as $K_n=A_n/i_{n\ max}$;

making a new n+1)-th measurement by generating a new (n+1)-th measurement curve and determining a new (n+1)-th maximum value $i_{n+1\ max}$; and, computing said portion of said substance of said gas sample for said new measurement from said new (n+1)-th maximum value $i_{n+1\ max}$ and said proportionality factor $K_n$ of said (n)-th measurement.

2. The method of claim 1, comprising the further steps of:

determining a new area $A_{n+1}$ from said new (n+1)-th measurement curve of said (n+1)-th measurement;

determining a new proportionality factor $K_{n+1}$ from said new area $A_{n+1}$ and said new (n+1)-th maximum value $i_{n+1\ max}$; and, computing the portion of said substance in said gas sample in a (n+2)-th measurement from the (n+2)-th maximum value $i_{n+2\ max}$ of said (n+2)-th measurement and said proportionality factor $K_{n+1}$.

\* \* \* \* \*